United States Patent [19]

Sneyd, Jr. et al.

[11] Patent Number: 4,710,185
[45] Date of Patent: Dec. 1, 1987

[54] FORAMINOUS NET COVER FOR ABSORBENT ARTICLES

[75] Inventors: James C. Sneyd, Jr.; Robert D. Harris, both of Cobb County; Margaret G. Latimer, Fulton County, all of Ga.

[73] Assignee: Kimberly-Clark Corporation, Neenah, Wis.

[21] Appl. No.: 931,952

[22] Filed: Nov. 20, 1986

Related U.S. Application Data

[63] Continuation of Ser. No. 775,480, Sep. 12, 1985, abandoned.

[51] Int. Cl.⁴ .............................................. A61F 13/16
[52] U.S. Cl. ...................................................... 604/372
[58] Field of Search ............... 604/372, 370, 371, 366, 604/367, 365, 358, 378

[56] References Cited

U.S. PATENT DOCUMENTS

| | | | |
|---|---|---|---|
| 3,193,604 | 7/1965 | Mercer | 264/209 |
| 3,394,431 | 7/1968 | Nalle, Jr. | 18/12 |
| 3,444,588 | 5/1969 | Martin et al. | 18/12 |
| 3,460,536 | 8/1969 | Champaigne, Jr. | |
| 3,554,853 | 1/1971 | Mercer et al. | 161/109 |
| 3,557,268 | 1/1971 | Beretta et al. | 264/145 |
| 3,618,609 | 11/1971 | Glick | |
| 3,678,933 | 7/1972 | Moore et al. | 604/372 X |
| 3,749,535 | 7/1973 | Gaffney et al. | 425/150 |
| 3,816,959 | 6/1974 | Nalle, Jr. | 47/23 |
| 3,882,871 | 5/1975 | Taniguchi | |
| 3,886,942 | 6/1975 | Bernardin | |
| 3,888,248 | 6/1975 | Moore | 128/156 |
| 3,917,889 | 11/1975 | Gaffney | 428/36 |
| 3,952,127 | 4/1976 | Orr | 428/255 |
| 3,988,410 | 10/1976 | Larsen et al. | 264/167 |
| 4,059,713 | 11/1977 | Mercer | 428/36 |
| 4,227,957 | 10/1980 | Keuchel et al. | 156/443 |
| 4,235,237 | 11/1980 | Mesek et al. | 604/372 |
| 4,304,234 | 12/1981 | Hartmann | 604/372 |
| 4,323,069 | 4/1982 | Ahr et al. | |
| 4,353,956 | 10/1982 | Nalle, Jr. | 428/255 |
| 4,399,184 | 8/1983 | Nalle, Jr. | 428/255 |
| 4,460,642 | 7/1984 | Errede et al. | 604/372 |

FOREIGN PATENT DOCUMENTS

| | | |
|---|---|---|
| 077034 | 4/1983 | European Pat. Off. |
| 097517 | 1/1984 | European Pat. Off. |
| 172420 | 2/1986 | European Pat. Off. |
| 844789 | 8/1952 | Fed. Rep. of Germany |
| 782504 | 9/1957 | United Kingdom |
| 810483 | 3/1959 | United Kingdom |
| 862112 | 3/1961 | United Kingdom |
| 970123 | 9/1964 | United Kingdom |
| 1110016 | 4/1968 | United Kingdom |
| 1158520 | 7/1969 | United Kingdom |
| 821959 | 10/1969 | United Kingdom |
| 1292133 | 10/1972 | United Kingdom |
| 1548865 | 6/1979 | United Kingdom |

OTHER PUBLICATIONS

Search Report from British Counterpart of above application (British Appln. No. 8622063).

Primary Examiner—John D. Yasko
Attorney, Agent, or Firm—Patrick C. Wilson

[57] ABSTRACT

An absorbent article (20) for proximate contact with a mammalian body adapted to receive a fluid containing discharge therefrom, includes an absorbent member (22) bearing a body-side cover (26) comprising a foraminous net (30) having a generally reticular network (32, 34) of polymeric filaments (36, 38). The net is comprised of two arrays of filaments oriented at a displacement angle ("a") in the range of 20°–90°. The cover is characterized by a basis weight of about 0.5–5.0 osy, a caliper of about 5–25 mils, an open area of about 30%–60% and a mesh of about 20–40. Individual filaments may have a size in the range of about 3–12 mils and may be superimposed or interlaid into the network.

41 Claims, 16 Drawing Figures

FORAMINOUS NET COVER FOR ABSORBENT ARTICLES .

This is a continuation of co-pending application Ser. No. 775,480, filed on 09/12/85, now abandoned.

TECHNICAL FIELD

The present invention relates, generally, to absorbent articles configured for proximate contact with a mammalian body in order to receive a fluid containing discharge therefrom, more especially to an improved body-side cover for such an absorbent article which has enhanced capabilities for transfer of fluid from the body to the absorbent matrix of the article, and more particularly to a cover as aforesaid which is comprised of a foraminous net having a generally reticular network of polymeric filaments. The improved cover of the present invention is particularly well suited for use in association with a wide variety of personal care articles such as bandages, as a liner for a disposable diaper or incontinent garment, and is specially adapted to serve as a cover for a tampon or a sanitary napkin.

DESCRIPTION OF THE BACKGROUND ART

All manner and variety of absorbent articles, and specifically those destined for use in personal care, are of course well known. The same are conventionally characterized as possessing an absorbent core or matrix having fluid retention properties, typically include a fluid impermeable back sheet which may or may not have vapor transport capabilities, and most often have a body-side cover or liner providing and interface between the article and the body to which it is applied. In this very general or conceptual sense, fluid discharged from the body is transported under pressure or by capillarity, or usually both, to the absorptive core or matrix wherein it is captured for ultimate disposal.

The outer covering, sometimes called a baffle or shield, normally is provided either to prevent soiling of contiguous clothing of the wearer, as when for example the absorptive article is a sanitary napkin or diaper, or indeed to prevent soiling of the body of the wearer beneath the area of contact with the absorbent article, as when for example that article is a wound dressing or bandage. Vapor permeability through the outer cover sheet oftentimes enhances comfort for the wearer as fluid within the absorptive core may evaporate and pass outwardly through the cover in exchange with the ambient. Regardless of the specific end to which the absorptive article is to be put, however, the same may function efficiently only to the extent that the fluid is transported across the interfacial cover or liner member into the core wherein it may be captured. Substantial advancements over the years have been made in improvements particularly directed toward increased absorbency and/or retentive capacities for the core or matrix material with the though in mind of improving the efficiencies of these personal care articles. For example, so-called superabsorbent materials are now conventionally added to disposable diapers or the like to replace a comparatively larger volume of wood pump fluff, theretofore customarily adopted as the absorbent material of choice. Fluid retention in the absorptive core and/or fluid distribution therein have both seen developmental efforts, for example, by the use of zoned absorbancy materials or designs. Yet, unless fluid is effectively transported to the core, the overall efficacy of the article itself is minimized.

Focusing on the role of a cover or liner member, perhaps no single application is as noteworthy for consideration as that for a sanitary napkin. Liners for disposable diapers or incontinent garments are capable of passing fluids such as urine with relative ease. The interfacial properties most commonly discussed relative to that setting include softness or lack of chafing irritability coupled with suitable hydrophobicity to maintain a relatively dry interface between the absorbent member containing the urine and the body of the wearer. Wound dressings likewise offer the personal care designer a relatively wide range of specific implementation options insofar as the interfacial member typically is considered successful provided it can pass excess exudate from the wound site while minimizing any tendency toward adherence between the bandage and that wound. Changing frequency also distinguishes these classes of personal care articles; diapers or incontinent garments are optimally changed relatively soon after the wearer has soiled the same, whereas wound dressings are typically considered to remain in place over a relatively much longer timeframe during the wound-healing process. To the very distinct contrary, sanitary napkins find themselves in a relatively singular class with all of these general thoughts borne in mind.

Further still along these lines, menstrual fluid is a physiologically complex composition as considered, for example, with regard to urine. In addition to uterine blood, menses contains cellular debris and a mucus-like fraction as well. The relative concentration of these components can and does vary widely among individuals, and in further point of fact, during different portions of the active menstrual cycle with regard to a given individual. Viscosity, volume and flow rate variations compound the complexity of the anatomical setting within which the sanitary napkin is required to perform. The situation is further exacerbated in light of psychological difficulties many women experience relative to the menstrual period. In this regard, visual perceptions of efficiency may well outweigh objective product performance in respect of the acceptability of a given product or in comparison with other like articles. Then too, as it is designed to be worn over a relatively long period, when considering the optimum changing frequency of a disposable diaper or incontinent garment, a sanitary napkin must receive and contain menses while offering the wearer a sense of confidence in the level of personal protection afforded and a feeling of comfort experienced during that time. Two somewhat subjective factors tend to dominate this perceptual aspect of efficacy—that the cover member is clean and dry. That subjective perception can be intensified where the cover further contributes to a more objective observation of physical separation between the body of the wearer and the absorbent matrix retaining the blood-laden discharge within the napkin structure; i.e., perception moves toward reality with the subjective view of isolation being reinforced by actual separation. This sense of physical separation or isolation is augmented in those instances where the cover provides a type of masking for that stain, reducing, for example, the color intensity from the typical blood red to a softer pink, approaching a whiter color.

Covers for sanitary napkins have historically been selected from a wide variety of materials and within a wide variety of configurations. Fabrics, both woven and nonwoven, have been used in the past as have films. Each offers one or more advantages commending its adoption as a cover for a sanitary napkin while each nonetheless retains significant drawbacks indigenous to either the material or form in which it is employed. For example, fabrics such as gauze were formerly a conventional cover material in the fabrication of sanitary napkins. Moving from those types of woven fabrics, the art adopted nonwoven products including spunbonded nonwovens, bonded carded webs, and the like. Manufactured from polymeric compositions which are either inherently hydrophobic or which can be treated to obtain that feature, these fibrous covers provide fair comfort to the user due to the fabric-like texture, hand and drape which can be imparted upon appropriate selection of materials and manufacturing techniques. Thus, for example, the cover disclosed in U.S. Pat. No. 4,397,644 is one which is extremely efficient in terms of wearer comfort and fluid transport into an absorbent core or matrix comprising the sanitary napkin. And yet, notwithstanding the significant stride forward represented by that variety of cover, the open fibrous network of such a nonwoven fabric does not achieve the dual objective of providing a clean and dry surface. For example, the fibrous network tends to trap menstrual fluid at or near the surface, not necessarily in a puddling sense but more in terms of capillary affinity, and thus the masking effect noted hereinabove is not achieved to the highest possible degree. Consequently, comfort is provided but the perceptual attributes—clean and dry—deemed important by many users are not completely attained. About the same may be said respecting the functionality of other nonwovens such as bonded carded webs or the like. The fibrous network characteristic of nonwovens militates strongly against an ability to meet the functional objectives of a dry, clean cover with adequate masking or observation of physical separation.

One may also profitably compare the wrapper disclosed in U.S. Pat. No. 3,460,536 with woven covers on the one hand and the foraminous net cover of the instant invention on the other. Designed as a conformable wrapper to envelop a sanitary napkin having an irregular shape, the cover of the U.S. Pat. No. 3,460,536 may be characterized as a woven or nonwoven mesh of yarns specifically configured to have tailored stretch characteristics to conform automatically to the shape of the pad. A first set of yarns, called the warp, is provided with relatively inextensible physical properties while a second set, dubbed the fill, are relatively stretchable. When assembled onto a pad, the inextensible warp threads prevent necking down of the cover under tension while the stretchable fill threads are unaffected by longitudinal tension but retain a good transversit fit. The patentee discloses the adaptability of natural or synthetic yarns, with threads in the 30 to 150 denier range being generally satisfactory. Thus, while such a cover works well for its intended purposes of conformability, it is not expected to provide the clean and dry surface sought after as optimal by many users of sanitary napkins, nor the important collateral attributes of actual and perceived separation/stain masking which constitute functional goals of the present invention.

Similar efforts to provide covers for sanitary napkins replacing gauze wrappers are memorialized in U.S. Pat. Nos. 2,900,980 and 2,902,037. Each discloses a wrapper consisting of textile or other threads extending both lengthwise and crosswise as in a woven gauze sheet. However, these threads are not interwoven or interlaced in the manner of gauze but are otherwise securely held in fixed relationship to one another in a very open mesh configuration, typically 4×4. In the case of the U.S. Pat. No. 2,900,980 approach, the wrapper is formed from a crosslaid thread backing or carrier web comprising a series of spaced, substantially parallel lengthwise extending threads and a series of spaced, substantially parallel crosswise extending threads, along with an applique of fibers. In a preferred mode, the mesh-like array resembling woven gauze is subjected to an adhesive bonding technique which likewise bonds the applique to the thread-formed web. The patentee notes various options, such as the orientation of threads into a more diamond-like array as well as an option for hot calendering, and particularly where a related option to utilize thermoplastic fibers or filaments is elected. For further insight into these types of covers, historically referred to as "scrim" covers, additional reference is made to U.S. Pat. Nos. 2,777,779, 2,841,202, and 2,902,395. While the cover members disclosed and claimed in these patent references constituted a significant step forward in the art at that time, the same did not address nor could they adequately provide a measure of adequate hiding power and separation as those objectives are defined and addressed herein; even further removed were capabilities along the lines of cleanness and dryness. The mesh networks involved were typically very open arrangements of very fine threads bearing low basis weight surface appliques of fibers, as envisioned clearly with reference to the figures of drawing laid out in the aforementioned patents. The thin comformable wrappers provided virtually no physical separation, whereas the intertwined applique of fibers within the mesh of the overall fabric structure would be found to retain fluid and substantial proportions of the more viscous components of the menstrual fluid to be passed. In sum, these types of wrappers filed to provide any meaningful measure of dryness, cleanness, and/or separation.

Other approaches have been attempted, wittingly or unwittingly with an effect of yielding a drier, cleaner cover than may be attained by a fibrous fabric structure. The use of plastic films which have been apertured in some fashion to permit fluid migration results in a cover which has a lesser tendency to retain or trap fluid on the surface due to the physical attributes of the film and, concomitantly, a lesser tendency toward cover staining. For example, the material disclosed in U.S. Pat. Nos. 3,929,135, 4,321,924, 4,323,069, 4,324,246, 4,342,314 and 4,463,045, collectively may be conceptually summarized as a polymeric film apertured to function as a cover for an absorbent article such as a sanitary napkin, wherein the hydrophobicity of the polymeric film coupled with the openings formed therein allow fluid to migrate through that cover into an absorbent matrix. As a plastic-based material, the sheen associated with these covers can be seen by many users as a drawback or psychological impediment, one which is attempted to be overcome by manufacturing techniques to create surface imperfections for light scattering purposes. Others have likewise employed plastic films such as those described in U.S. Pat. Nos. 3,137,746, and 3,434,472. Again, simply looking at the conceptual approach adopted, a thermoplastic film is slitted or otherwise pierced or embossed and then is stretched to open up the film by providing an array of apertures through which fluid may pass. (See also, GBA Pat. No.

2,085,035.) Materials of this ilk have found their way into the commercial marketplace as covers on sanitary napkins. However, regardless of the approach, these sorts of film possess inherent limitations much as the case with respect to fabric or more fabric-like covers mentioned above; albeit, in this setting those limitations are different ones. For example, the film network remaining after piercing, embossing, or otherwise creating the apertures through which fluid will pass typically must constitute the major or nearly the major surface area for the cover inasmuch as the formation of too great a number of size of apertures collectively reduces the structural integrity of the cover. Thus, there are limitations in respect of the manner in which forces are transferred and/or resolved throughout the plane of the cover web as an antagonistic consideration relative to the objective of having a relatively open cover structure for passing menstrual fluid; a feature perhaps more important in the manufacturing stage than use, but one the significance of which should not be underestimated. Thus, cover integrity may well be a tradeoff depending upon design where one wishes to provide an open array for passage of all components of menstrual fluid. Then as well, from the subjective or psychological point of view, many individuals are disinclined to utilize an article such as a sanitary napkin bearing a plastic film cover. Further processing steps to ameliorate the plastic glare of the film are then required, the increased manufacturing costs associated therewith being a tradeoff against use of these films.

As can now readily be appreciated, the historical approach to designing cover members for absorbent articles and most notably sanitary napkins, has been a matter of concession. Comfort, cleanliness, dryness, and other perceptual features such as masking, having often been compromised, one against another, due to an inability to attain optimal performance for a cover across the spectrum of desired functional goals, and, to the extent that the art has responded to date, those responses have necessitated relatively complicated and-/or costly measures. Accordingly, the need exists to provide a simple yet highly efficient cover which is both easy to manufacture and to associate into a finished article while highly efficacious in use.

Disclosure of the Invention

The present invention concerns a cover, ideally suited for use as a sanitary napkin cover, designed with the foregoing thoughts in mind. The cover of the present invention advantageously provides enhanced interfacial characteristics between the absorbent core destined to receive a discharge or exudate from a body and the surface of the body itself. The cover is desirable for its ability to transmit fluid, and in the case of menses, the more viscous mucous or squamous cell components as well, while maintaining a dry and clean interface at the surface of the wearer's body. In considering particularly its role as a cover for a sanitary napkin, this component also is capable of providing a highly desirable degree of physical separation, both perceived and real, between the menstrual fluid retained within the core of the napkin and the wearer, masking to a high degree the stain of the core created by captured menses. Yet, these attributes are achieved with the added benefit of a comfortable cover member, which may retain a high level of open area and which does not contribute to undue chafing. Those advantages are realized with the further benefit of efficiency of manufacture, both in terms of fabrication of the cover itself and then, equally importantly, its association with the remaining components comprising the absorbent article.

The foregoing, and other advantages as well, are accomplished in one aspect of the present invention by means of a cover comprising a foraminous net having a generally reticular network of polymeric filaments, most preferably monofilaments. The reticular network is preferably comprised of first and second arrays of filaments disposed generally parallel to one another within each array and at a displacement angle between respective arrays to achieve the net configuration. In one implementation of the present invention, the first array of filaments is superimposed at the appropriate displacement angle over the second array of filaments, whereby the network is comprised of generally overlapping polymeric filament arrays. In an alternative implementation, the first array of filaments is interlaid at the displacement angle within the second array of filaments, whereby the network is comprised of generally intersecting polymeric filament arrays. The geometry of the foramina may be varied widely depending upon the displacement angle elected; the displacement angle preferably lying within the range of from about 20° to about 90°, more preferably in the range of from about 40° to about 70°, and most preferably in the range of from about 45° to about 55°. Although overall the geometry of the foramina is best described as rectilinear, it is preferred that the intersections of filaments constituting the arrays be achieved to promote the formation of a fillet at each of the junctures in order to reduce the tendency for capillary affinity thereat and collateral fluid retention in the cover. The cover of the present invention enjoys a strength advantage over many other polymeric covers which indeed can be the source of considerable benefit in manufacturing due to the manner in which forces are distributed and the ability to tailor that distribution of force along the networks of continuous filaments. Regardless of absolute strength comparisons, it is also to be expected that the net cover of the present invention, in its preferred form, will enjoy a comparable toughness advantage (determined as the area lying below a normal stress-strain curve) over other polymeric covers. In turn, these physical attributes promote an ability to manufacture the cover within a wide range of basis weights depending upon the immediate requirements at hand as established by the designer. Thus, the cover of the present invention may have a basis weight within the range of from about 0.5 to about 5.0 ounces per square yard ("osy"), more preferably with regard to a sanitary napkin within the range of from about 1.0 to about 2.0 osy, and most preferably a basis weight of about 1.0 osy. Likewise, the caliper of the cover of the present invention may be selected within rather broad bounds in the range of from about 5 to about 25 mils (i.e., thousandths of inches), more preferably in the range of from about 8 to about 17 mils, and most preferably in the range of from about 10 to about 13 mils. The caliper can be reduced without an unacceptable tradeoff in strength by means of post fabrication treatments such as, for example, calendering. In such a case, the cover of the present invention may be a calendered net having a caliper in the range of from about 5 to about 10 mils as the result of a smooth calendering operation; however, patterned calendering or embossing will increase thickness or caliper. The inherent integrity of the cover of the present invention further contributes to an ability to have a much greater open area than heretofore attainable by most, if not all, conventional cover stocks. Thus, although greater open areas may be utilized, when designing with an eye toward a cover for a sanitary napkin the open area of the network may lie within the range of from about 30% to about 60% relative to the area of the entire net, more preferably in the range of from about 40 to about 55%, and most preferably in the range of from about 48% to about 52%. When a post treatment is employed as summarized very briefly above, a, e.g., smooth calendered net cover may employ a network having an open area in the range of from about 20% to about 50%, more preferably in the range of from about 30% to about 45%. The mesh of a net in accordance with the present invention advantageously lies in the range of from about 20 to about 40 (measured orthogonally as strands per inch), more preferably in the range of from about 25 to about 35 and most preferably in the range of from about 30 to about 32. The cover may have biaxial symmetry with regard to the mesh parameter or each of the arrays constituting the network may have an independently variable mesh count within the aforementioned ranges. Thus, the mesh count of the net may be the same or it may be different in each array of filaments. The individual filaments themselves may have diameters (where circular or nearly so) or major aspect dimensions (where noncircular) in the range of from about 3 to about 12 mils. As with the case of mesh, the dimensions of the filaments may vary among those filaments comprising a given array or between arrays themselves. Thus, for example, smaller filaments of a first mesh count may be superimposed over larger filaments of a second mesh count in order to tailor fluid flow depending upon the nature of that fluid; and similarly, filaments within one array may have differing diameters inter se in order to present a more fabric-like appearance, particularly where one elects a superimposed filamentary network and it is the upper of the two arrays which is so designed. In this regard, considering the available options outlined in summary fashion immediately above, the net cover of the present invention advantageously may be designed to have generally isotropic symmetry of physical properties with suitable anisotropy in respective physical characteristics (e.g., stretchable in several directions, but to differing degrees).

The net which constitutes the cover of the present invention is most preferably fabricated from a polymeric composition selected from the group consisting of the extrudable ethylene vinyl acetates, polyolefins such as polyethylenes and polypropylenes, polyesters, nylons and appropriate blends thereof. Most preferred is ethylene vinyl acetate and, even more specifically, one having from about 2% to about 22% vinyl acetate with a decided preference toward the upper end (e.g., 17-18%), although the polyethylenes may well offer the fabricator certain advantages with regard to production rates, softer fabric hand and raw material costs. Optionally, but preferably a pigmenting agent is also added to the composition, such as, for example, up to about 20% titania, to aid in the masking effect sought to be achieved by the instant cover.

The filaments, depending upon composition, are most preferably monofilaments formed in a desired cross section selected from the group of geometries consisting of circular, ovate, triangular, square, rectangular, and "T" shaped geometries or suitable combinations or modifications thereof. Where the superimposed filamentary arrays are selected any of these geometries will be found to be readily workable in the fabrication of a net; albeit, the more regular geometries and especially the arcuate ones will typically be the better when the interlaid filamentary network is preferred. Further along the same lines, depending upon the interrelationship between arrays of filaments, those in one array may assume the same or different geometry as respects those of the other array.

Other aspects of the present invention as well as an appreciation for the manner in which it is implemented and the aforementioned advantages achieved, will become apparent upon an examination of the ensuing detailed description of the best modes for carrying out the same taken in conjunction with the figures of drawing.

DETAILED DESCRIPTION OF THE INVENTION AND BEST MODES FOR IMPLEMENTING THE SAME

The present invention relates, generally, to absorbent articles configured for proximate contact with a mammalian body in order to receive a fluid containing discharge therefrom, more especially to an improved body-side cover for such an absorbent article which has enhanced capabilities for transfer of fluid from the body to the absorbent matrix of the article, and most particularly to a cover as aforesaid which is comprised of foraminous net having a generally reticular network of polymeric filaments. The improved cover of the present invention is particularly well suited for use in association with a wide variety of personal care articles such as bandages, as a liner for a disposable diaper or incontinent garment, and is especially adapted to serve as a cover member for a tampon or a sanitary napkin. Accordingly, while the present invention will now be described with reference to certain preferred embodiments within the aforementioned contexts, emphasizing its utility as a sanitary napkin cover, those skilled in the art will appreciate that such a description is meant to be illustrative only and not limitative with regard to the scope thereof.

Figure 1:
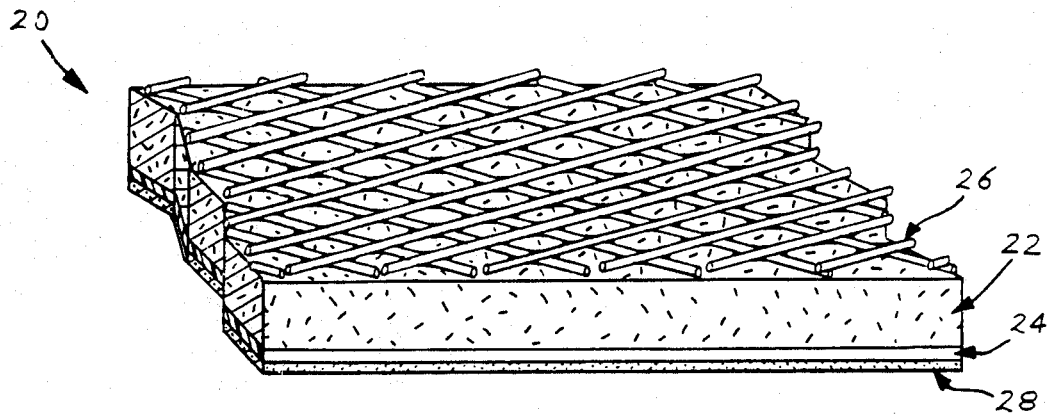
FIG. 1 is an isometric sectional view, with parts broken away, showing an absorbent article incorporating a cover in accordance with the present invention.

Turning to the figures of drawing, in each of which like parts are identified with like reference characters, FIG. 1 illustrates a sanitary napkin designated generally as 20 comprised in its most fundamental aspects of an absorbent core or matrix 22 disposed intermediate a baffle 24 and a cover 26. The baffle is shown bearing a garment suspension adhesive 28 as is generally conventional, to secure the sanitary napkin to the garment of the wearer. The absorbent core may be comprised of any of a number of materials typically used for that purpose, such as wood pulp fluff, creped wadding, coform (a physical association of pulp fluff and meltblown filaments) or such other equivalent material as may be regarded appropriate for containing menstrual fluid. Of course, if a different application is desired, a different absorbent may be deemed more useful. Regardless, the baffle 24 serves as a containment member for the sanitary napkin 20, both protecting the garments of the wearer against strike-through from the rear side of the napkin and also as a convenient substrate on which to dispose the suspension adhesive noted above. the cover 26, for purposes pertinent here, is the focus of the present invention inasmuch as it provides the interfacial member between the sanitary napkin 20 and the body of the wearer, through which menstrual fluid must pass in order for the napkin to function properly and efficiently for its intended purpose, and one which also effects stain masking of the fluid captured within the absorbent cover. As used, herein, that term "masking" is meant to connote the ability of the cover to reduce the color, intensity or hue of the stain of the absorbent core. The cover 26 illustrated here for those particular purposes is shown to be in the form of a foraminous net identified generally as 30 in FIG. 2 and described in greater detail below.

The targeted attributes or benefits sought to be optimized by the cover 26 of the present invention is that it be clean, dry and soft or comfortable while yielding its masking effects. The cleanliness objective is approached by providing a surface which is non-trapping as respects both fluid and debris within the menstrual fluid while providing the wearer a measure of separation between her body and the absorbent core or matrix 22. Dryness, as a functional objective, is sought to be obtained by providing a fast strikethrough the cover so that the menstrual fluid may rapidly be wicked and retained within the core 22 while also providing a degree of separation between the body of the wearer and that fluid laden core. Softness is provided by a flexible, compressive cover which is yielding, and particularly so during normal movements of the wearer. These functional objectives are attained by tailoring specific attributes of the net 30 in order for it to function as a cover for the sanitary napkin 20.

Figure 2:
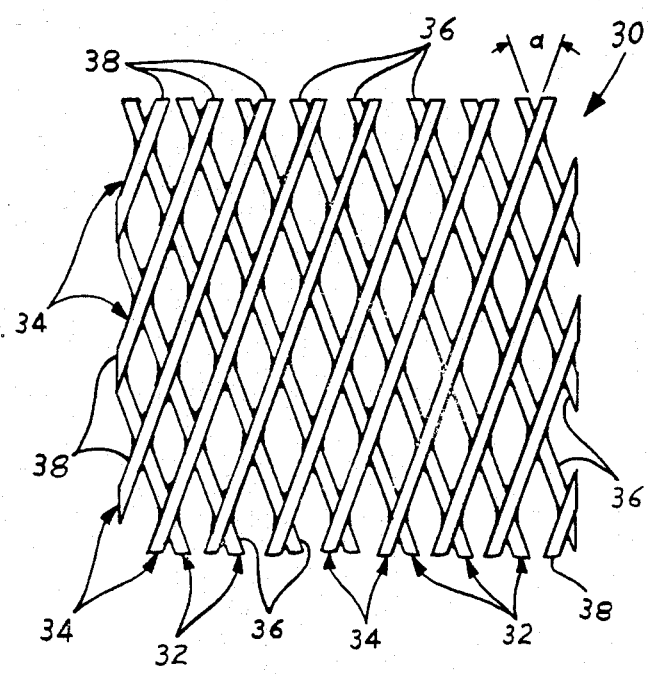
FIG. 2 is a fragmentary top plan view of a cover in accordance with the present invention, shown here as a reticular net having generally diamond shaped foramina.
Figure 3:
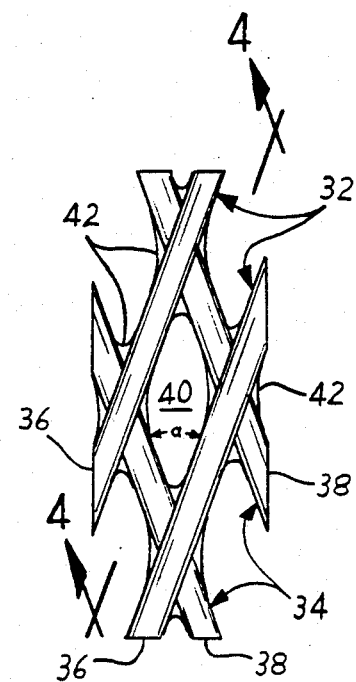
FIG. 3 is a much enlarged plan view of a portion of the filamentary network comprising the cover shown in FIG. 2.
Figure 4:
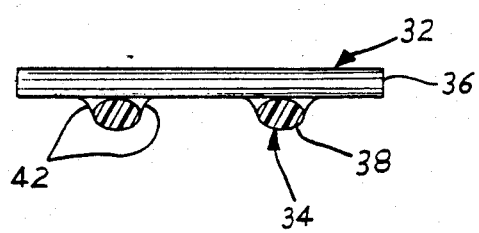
FIG. 4 is a sectional view taken substantially along the line 4—4 of FIG. 3.

Turning to the net 30 depicted in FIGS. 2-4, the same is generally shown to be comprised of a first array of filaments 32 disposed at a displacement angle "a" relative to a second array of filaments 34. Each of the arrays 32 and 34 is comprised of a plurality of individual filaments, 36 and 38 respectively. Within each array, e.g., 32, the individual filaments, i.e., 36, are most preferably generally parallel one to another so that a conventional reticular network is formed by the association of the two arrays 32 and 34 at the displacement angle "a". The displacement angle is variable over a fairly wide range of from about 20° to about 90°, whereby the shape of the individual foramina 40 may be varied. Likewise, altering the angular displacement between filaments comprising the network varies the distribution of forces in the cover 26, which can be tailored by resolving them through the reticular network of the web. This latter feature can become a concern, and turned to good advantage, particularly in the manufacturing stage of a sanitary napkin 20 (or like absorbent article) depending upon the machine direction relative to the axial array of the net 30 and the vectorial displacement of manufacturing forces throughout that web. Those strength considerations imply several additional benefits in terms of an ability to provide more widely open area for the cover and do so with a reduced basis weight as will become more apparent as the present description continues.

Within the broad range of displacement angles noted immediately above, the angle "a" more preferably lies within the range of from about 40° to about 70° and most preferably in the range of from about 45° to about 55° when the net 30 is destined for use as a cover for a sanitary napkin. Thus, the individual foramina 40 take on a generally rectilinear shape in this case resembling most closely a diamond-shape as best viewed in FIG. 3. Depending upon the character of the fluid to be passed by the cover 30, the size and shape of the filaments comprising the same, and the material(s) from which it is manufactured, there may under certain circumstances be some fluid affinity for the cover based upon its own surface energy and the wetting angle relative to the displacement angle. Inasmuch as the attributes of cleanliness and dryness are maximized with a non-fluid-trapping cover, it is preferred that the cover be treated with these thoughts in mind in order to minimize, if not eliminate altogether, that type of fluid affinity. In many instances it may be appropriate simply to apply a suitable surface active agent and thereby render the cover material sufficiently hydrophobic to preclude trapping of fluid via capillarity such as may occur particularly within the acute angle region of the foramina 40. It is equally well envisioned to form the net 30 to include fillets 42 at each juncture as best viewed in FIGS. 3 and 4 in order to minimize the otherwise more radical angular orientation between those filaments in array 32 and the complementary array 34. Consequently, when adopting the fillet approach to reducing capillary affinity of the net cover, the overall rectiliner filament array or orientation is mediated toward a more arcuate foramina array or orientation, as best envisioned with regard to FIG. 3 wherein central foramen 40 is shown as a generally elliptical one. Irrespective of the approach, however, the objective remains the reduction of trapping tendencies which would otherwise make more difficult attaining the objectives of a clean, dry cover for the sanitary napkin 20, whether it be by chemical or physical means.

As noted generally above, the ability to alter the displacement angle contributes to the ability to tailor force distribution within the web constituting net 30. Depending upon the choice of materials for the net, and given the fact that the filamentary nature of the network allows for this resoltuion of forces more efficiently than might be attained through use of a film or more fabric like structure, a wide range of basic weights is useful in the design of an absorbent article having a cover in accordance with the present invention. Broadly speaking, a useful basis weight will range in practical terms from about 0.5 to about 5.0 ounces per square yard ("osy"). Obviously, webs with a lower basis weight may be adopted in cases where the more fragile network is either otherwise acceptable or is offset by the adoption of a material which is somewhat stiffer, recognizing a potential collateral reduction in softness. For most cases involving applications for sanitary napkins or the like, basis weights below 0.5 osy will, however, be found to lack one or more of the features necessary to attain a clean, dry and soft cover; for example, both perceived and actual separation may be found to be insufficient as compared wtih an ideal model once basis weights are reduced below about that minimal level. Likewise, basic weights in excess of about 5.0 osy imply a cover which tends toward too great a stiffness, thus yielding a harsher cover stock which would, for that reason, normally be deemed unacceptable. However, in other contexts, a cover having a basis weight considerably greater than 5 osy may be deemed acceptable by the designer.

The foregoing is, as will be appreciated by those skilled in the art, interrelated with the caliper of the net 30. In the embodiment viewed in FIGS. 3 and 4, wherein the first array of filaments 32 is superimposed over the second array of filaments 34, caliper is measured across the junctures tangent to the pairs of filaments constituting the web. In other embodiments, caliper will be deemed herein to be the measure of the greatest transverse aspect of the web regardless of physical conformation of either the filaments or their association into the net 30. Withthat privisio, nets especially adaptable for use as covers for a sanitary napkin may have a caliper in a range of from about 5 to about 25 mils (i.e., thousandths of inches). Much as with the case of basis weight, nets having thinner or thicker dimensions will ordinarily be found to be too fragil or lack adequate masking at the low end or be too stiff and harsh at the high end. Within those broader bounds, covers for sanitary napkins are most preferably comprised of nets having a caliper in the range of from about 8 to 17 mils and most preferably from about 10 to 13 mils. In certain cases it has been found that post fabrication treatments for a net 30, prior to its association with the other constituents of the sanitary napkin 20, may improve, inter alia, its aesthetics. One such envisioned operation is a (smooth) calendering of the net, which provides not only a somewhat smoother texture but improves flexibility, reduces open area and permeability and adjusts strike-through rates and rewet values. In such cases, the cover in the form of calendered net may thus have an equivalently reduced caliper due to the transverse compression of the filaments toward the low end of the broader range, in this instance a calendered net cover having a caliper in the range of from about 5 to about 10 mils being most preferred.

As is further apparent to those skilled in the art, basis weight and caliper both are functions of the dimensional aspect of the individual filaments constituting the net 30. All other things being equal, a nominal dimension for each of the filaments 36 and 38 is in the range of from about 3 to about 12 mils. In those cases where the filaments are circular or nearly so, that would be deemed a diameter measurement. In those instances where the geometry of the filament(s) is a noncircular one, such as represented in the exemplary cross sections of FIG. 5, this measurement is taken as the major dimensional aspect of the respective geometric shape along the axis normal to the plane of the net 30. Thus, for the ovate cross section of FIG. 5B, in the orientation shown, the dimension would correspond to the minor axis of the ellipse whereas, were the filament represented by FIG. 5B rotated 90° and a net 30 fashioned from a filament of that orientation, the measurement would be along the major axis of the ellipse.

The percent open area of the net 30 is an important parameter is assessing its overall functionality. Dryness of a cover, and particularly one for a sanitary napkin is an indirect function of the speed with which fluid may pass through that member into the absorbent core. In turn, the more open the network the more rapidly fluid may strike through the cover, recognizing of course the compromise with regard to masking the stain within the core, a matter considered in somewhat greater detail below. Also related to a consideration of the percent open area is the structural integrity of the cover, both during the fabrication stage and then later in use. As opposed to films, where too great an open area tends to diminish the strength and resistance against tearing, the percentage open area which may be achieved using the filamentary network of the net 30 is proportionately increased and especially where the open area begins to exceed about 50%. For use as a cover member for a sanitary napkin, the percentage open area for cover 30 may vary widely within the range of from about 30% to about 60%, more preferably it is maintained within the range of from about 40% to about 55%, and most preferably between about 48% and 52%. As related briefly above, nets destined for use as sanitary napkin covers in accordance with the present invention oftentimes will be treated by means of, e.g., calendering in order to smooth the web. In those cases there will be seen a concomitant decrease in percent open area; for a smooth calendered net, one having an open area in the range of from about 20% to about 50% or more preferably in the range of from about 30% to about 45% is deemed highly efficacious.

Figure 6:
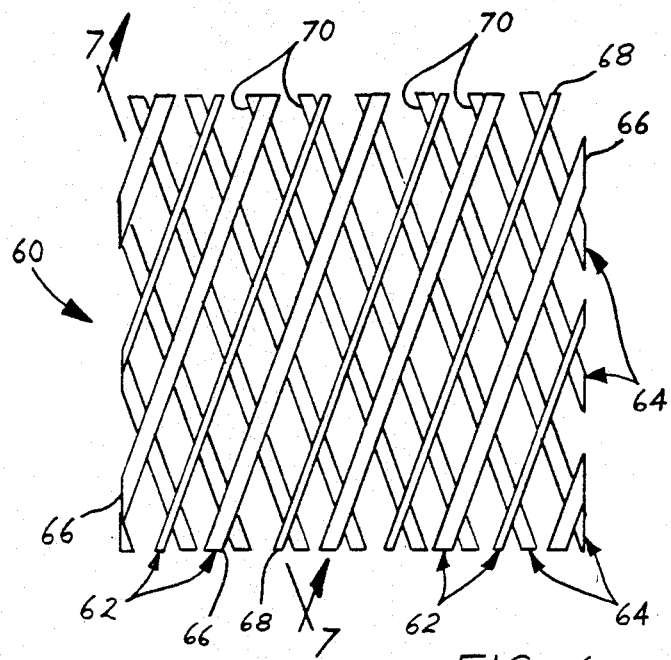
FIG. 6 is a top plan view, similar to FIG. 2 but showing still a further alternative in the association of filaments with an eye toward creating a more fabric-like appearance for the cover member.
Figure 7:
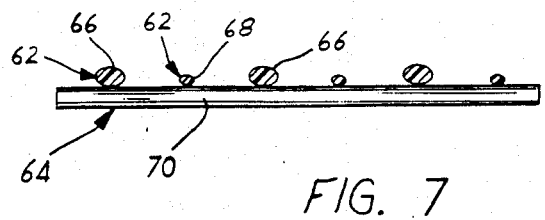
FIG. 7 is a sectional view taken along the line 7—7 of FIG. 6, showing three separate junctures for a cover similar to the one of FIG. 4.

The mesh of the net 30 is variable depending upon the character of the fluid to be passed. When considering the design of a net as a cover for a sanitary napkin, the mesh may vary within the range of from about 20 to about 40, more preferably from about 25 to about 35, and most preferably from about 30 to 32, these representing a measure of the number of strands per inch of net counted in a direction normal to the filament axis of the measured array. Thus, for example, the mesh count for the array 32 comprising those filaments 36 would be a measure of the number of strands per inch in the direction identified "A" in FIG. 2, whereas the mesh count for the array 34 would determine the number of strands per inch in the direction "B". It has been determined that there is no requirement for biaxial symmetry with regard to this mesh count. Thus, whereas the mesh may be the same in each of the A and B directions (e.g., 30×30), it is equally well envisioned that the mesh counts may differ for each of the two arrays (e.g., 30×40—indicating a somewhat more open network for the array 32 than 34). It has further been determined that the individual filaments within a given array may vary in size. For example, as may be seen with reference to FIGS. 6 and 7, a net 60 is shown to be comprised of a first array 62 and a second array 64, the former superimposed on the latter as best viewed in FIG. 7. The filaments comprising array 62 include filaments 66 having a first diameter and filaments 68 having a second, in this case lesser diameter; whereas those filaments 70 comprising the array 64 are all of the same physical size. Although FIG. 7 illustrates a symmetric disposition of the filament 66 and 68, this too may show some pattern or variation in repeat or indeed may be quite random at the desires of the designer. By an appropriate selection and intermixture of sizes and mesh counts for each array relative to the other, one may be suitable material selection provide a very fabric-like appearance to what is otherwise a polymeric network of filaments. Hand, drape, and other tactile properties may be designed in order to approach more closely the feel and appearance of a fabric and its associated comfort while maintaining the cleanliness and dryness heretofore unattainable with, e.g., nonwovens.

Just as size and placement of filaments may vary in accordance with the immediately aforesaid, so too may the mixture of geometric shapes. Although the nets depicted in the FIGS. 2-4 and 6-7 are comprised of generally circular filaments, any of the geometries illustrated in FIG. 5 may equally well be employed. Indeed, depending upon the method of manufacturing the net, a matter considered briefly below, other shapes are adaptable to the manufacture of cover nets in accordance with the present invention. Thus, for example, the circular cross section of FIG. 5A may be adapted to an ovate filament as represented in FIG. 5B. More angular geometries such as triangular, square or rectangular as depicted in FIGS. 5C-5E are within the scope of the present invention. A "T" geometry as shown in FIG. 5F is particularly preferred with an eye toward reduction of material as those skilled in the art will appreciate by the circular geometry shown in phantom lines circumscribing that filamentary geometry. It is also considered within the scope of the present invention to merge some of the more rectilinear cross sectional geometries with some of the more arcuate. Along these lines, FIG. 5G represents a generally rectangular cross section with arcuate sides whereas FIG. 5H is more in the anture of a trapexoidal cross section with arcuate or rounded sides. Some of these shapes may be more readily attainable depending upon the manner of manufacture of the net than others; and depending upon the purpose to which the same is put; some geometries may be more or less commendable. In addition to basis weight reductions, for example, one may achieve more textile-like appearances and hand, improved masking, separation, rewet and comfort characteristics with judicious selection and mix of filament sizes and shapes.

Figure 5A:
FIG. 5 illustrates several optional cross sectional geometries, identified A-H, suitable for use as filament cross sections for a cover in accordance with the present invention.
Figure 5B:
Figure 5C:
Figure 5D:
Figure 5E:
Figure 5F:
Figure 5G:
Figure 5H:
Figure 8:
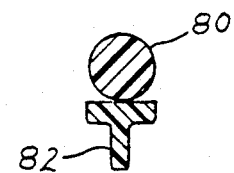
FIG. 8 is a sectional view through one juncture of a net made in accordance with the present invention, illustrating here the manner in which different cross sectional geometries may be associated; and, FIG. 9 is a sectional view, similar to FIG. 4, but showing in this instance an alternate implementation of a filamentary network in accordance with the present invention adapted for use as a cover such as the one depicted in FIG. 2.

Carrying these same concepts further, FIG. 8 illustrates a single juncture of a net wherein the upper array of filaments, here denoted simply 80, of a cross sectional geometry deemed generally circular in accordance with that of FIG. 5A is shown superimposed on an array with a generally "T" geometry as shown in FIG. 5F, identified as 82. As is the case in respect of filament size, it is sometimes advantageous to adopt differing geometries for the filaments comprising the independent arrays which, overall, define the reticular network. In this instance the use of a T-shaped filament within the lower array accounts for savings in weight and material whereas the use of a more arcuate geometry for the upper array maintains the smoother feel for the network. Thus, in this instance, the upper array 80 would be that toward the body of the wearer while the lower array 82 would face the absorbent matrix.

Figure 9:
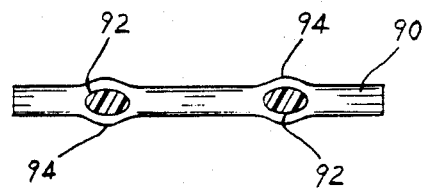

The nets heretofore described have been done so in respect of upper and lower arrays as best viewed, for example, in FIGS. 4 and 9. This yields a net structure of generally overlapping filamentary arrays. However, it is equally well possible to form a net with interlaid arrays of filaments such as that best viewed in FIG. 9. In this embodiment a first array of filaments denoted 90 will be found to be intersecting relative to a second array of filaments denoted 92, the same separated by an analogous displacement angle to yield the net structure. In such an instance there will be some tendencies toward the formation of fillet-like junctures at the points of intersection of the filaments 90 and 92, represented as 94 in FIG. 9. Otherwise, the net will tend to function in virtually the same way as a net of superimposed filaments although, depending upon material selection, the knuckle-like junctures 94 may have a tendency to contribute to somewhat greater overall stiffness.

The covers of the present invention may be fabricated in any convenient manner from readily available material. It is preferred, however, to manufacture these nets by means of extrusion formation techniques employing materials which are both extrudable on the one hand and provide appropriate tactile qualities on the other. These materials include the extrudable ethylene vinyl acetates, polyolefins such as polyethylenes and polypropylenes, polyesters, and nylons, as well as suitable blends thereof. Most preferred are the ethylene vinyl acetates having from about 2% to about 22% vinyl acetate, with a particular preference for an EVA with about 17-18% vinyl acetate content in the copolymer. Under some circumstances, polyethylenes may offer certain advantages over EVA, providing potential opportunities for faster production rates, softer fabric hand and lower raw material costs. Regardless of specific selection, such materials are then most preferably coextruded through counter-rotating die tips utilizing apparatus and processes such as those discussed in U.S. Pat. Nos. 3,620,883, 3,616,080, and 3,560,306 and the related patents referenced therein. Simply stated, a first array is extruded through a first rotating die and the second array is nearly simultaneously extruded through a second concentrically rotating die; the two separate arrays then being married one to another while the extruded polymer remains in a tacky state. This achieves both adhesion of filaments one to another and, depending on appropriate process control (well within the skill of those in the art), provides both a measure of control over the geometry of the net foramina and filaments (a function of die geometry as well as physical properties of the extruded polymer) and the formation of the fillets 42 noted above. However, those skilled in this art will appreciate that there are various other techniques which might equally efficiently be employed for fabrication of a net such as the one described herein.

A net made in accordance with the foregoing preferred embodiments has been found to function highly efficaciously as a cover member for a sanitary napkin. No trapping pores will be found on the surface of the net while the same will be seen to pass fluid rapidly and efficiently therethrough into the absorbent core or matrix of a sanitary napkin. Good perceptual and physical separation is seen while comfort is maintained. Furthermore, masking of the stain normally associated with the use of a sanitary napkin may be intensified by the addition of a minor amount of pigmenting agent to improve the whiteness of cover, for example, the addition of up to about 20% titania for that purpose. Indeed, in its preferred form, a net cover made in accordance with the present invention achieves a fiveto six-fold improvement over scrim covers for sanitary napkins with regard to stain masking capabilities, reducing the intensity and hue of menses from bright red to pin—i.e., the peak in spectral distribution is reduced (intensity) and the distribution broadened (hue). Accordingly, the present invention will be seen to respond to the needs of the prior art in each of the areas of cleanliness, dryness and comfort; while, at the same time these objectives are achieved by means of a web which is easily and economically fabricated and which is very efficiently associated with the other components constituting the absorbent article.

While the invention has now been described with reference to certain preferred embodiments, and exemplified in many respect thereto, those skilled in the art will appreicate the various modifications, substitutions, change and omissions may be made without departing from the spirit thereof. For example, in addition to or in place of titania as a pigmenting agent, other such ancillary components may be included for stain-masking objectives. Likewise, the filaments comprising the foraminous net cover of the present invention may be modified chemically to impart desired physical properties; e.g., foaming agents may be included to foam the filaments and thereby achieve some improvements in dry fabric hand while reducing basis weight. Other adjuvants may similarly be added to alter the physical properties of the net to adapt it more specifically to the purpose for which it is to be used. Accordingly, it is intended that the foregoing description be deemed merely illustrative of certain preferred modes for making and using the present invention and not be deemed limitative on the full scope thereof.

What is claimed is:

1. An absorbent article for proximate contact with a mammalian body adapted to receive a fluid containing discharge therefrom, including an abosrbent member bearing a clean, dry body-side cover as an interfacial fluid transfer and stain masking member, said cover comprising a foraminous net having a generally recticular network of first and second arrays of continuous polymeric monofilaments disposed generally parallel one to another within each of said arrays and at a displacement angle between respective arrays.

2. The absorbent article of claim 1, wherein said first array of filaments is superimposed at said displacement angle over said second array of filaments whereby said network is comprised of generally overlapping polymeric filament arrays.

3. The absorbent article of claim 1, wherein said first array of filaments is interlaid at said displacement angle within said second array of filaments whereby said network is comprised of generally intersecting polymeric filament arrays.

4. The absorbent article of claims 1, 2 or 3, wherein said displacement angle is in the range of from about 20° to 90°.

5. The absorbent article of claim 4, wherein said displacement angle is in the range of from about 40° to about 70°.

6. The absorbent article of claim 3, wherein said displacement angle is in the range of from about 45° to about 55°.

7. The absorbent article of claims 1, 2 or 3 wherein said cover has a basis weight in the range of from about 0.5 to about 5.0 ounces per square yard (osy).

8. The absorbent article of claim 7, wherein said cover has a basis weight in the range of from about 1.0 to about 2.0 osy.

9. The absorbent article of claim 7, wherein said cover has a basis weight of about 1.0 osy.

10. The absorbent article of claims 1, 2 or 3, wherein said cover has a caliper in the range of from about 5 to about 25 mils.

11. The absorbent article of claim 10, wherein said cover has a caliper in the range of from about 8 to about 17 mils.

12. The absorbent article of claim 10, wherein said cover has a caliper in the range of from about 10 to about 13 mils.

13. The absorbent article of claim 10, wherein said cover is a calendered net cover having a caliper in the range of from about 5 to about 15 mils.

14. The absorbent article of claims 1, 2 or 3, wherein the open area of said network is in the range of from about 30% to about 60% relative to the area of said net.

15. The absorbent article of claim 14, wherein said open area is in the range of from about 40% to about 55%.

16. The absorbent article of claim 14, wherein said open area is in the range of from about 48% to 52%.

17. The absorbent article of claims 1, 2 or 3, wherein said cover is a calendered net cover having an open area of said network in the range of from about 20% to about 50% relative to the area of said calendered net.

18. The absorbent article of claim 17, wherein said open area is in the range of from about 30% to about 45%.

19. The absorbent article of claims 1, 2 or 3, wherein the mesh of said net is in the range of from about 20 to about 40.

20. The absorbent article of claim 19, wherein said mesh is in the range of from about 25 to about 35.

21. The absorbent article of claim 19, wherein said mesh is in the range of from about 30 to about 32.

22. The absorbent article of claim 19, wherein the mesh count of said net is the same in each array of filaments.

23. The absorbent article of claim 19, wherein the mesh count of said net is different in each array of filaments.

24. The absorbent article of claims 1, 2 or 3, wherein the diameter of said filaments is in the range of from about 3 to about 12 mils.

25. The absorbent article of claim 24, wherein a preselected number of said filaments differ in diameter from the remainder comprising said net.

26. The absorbent article of claim 24, wherein the filaments comprising one filamentary array of said net have a first diameter and the filaments comprising the other array have a second diameter different from said first diameter.

27. The absorbent article of claims 1, 2 or 3, wherein said net is fabricated from a polymeric composition selected from the group consisting of the extrudable ethylene vinyl acetates, polyolefins, polyester, nylon and mixtures thereof.

28. The absorbent article of claim 27, wherein a pigmenting agent is added to said composition.

29. The absorbent article of claim 28, wherein a pigmenting agent is comprised of up to about 20% by weight $TiO_2$.

30. The absorbent article of claims 1, 2 or 3, wherein said filaments have a cross section selected from the group of geometries consisting of circular, ovate, triangular, square, rectangular and "T" shaped geometries and mixtures thereof.

31. The absorbent article of claim 30, wherein said filaments have an arcuate geometry.

32. The absorbent article of claim 30, wherein the foramina of said net are generally rectilinear and the intersection of said filaments have interior fillets.

33. The absorbent article of claims 1, 2 or 3, wherein said net is an extruded net.

34. The absorbent article of claims 1, 2 or 3, wherein said net is comprised of a network of polymeric monofilaments.

35. A sanitary napkin having a body-side cover consisting essentially of a foraminous net having a generally reticular network of first and second arrays of generally parallel continuous polymeric monofilaments within each of said arrays, oriented at a sisplacement angle between arrays in the range of from about 20° to about 90°.

36. The sanitary napkin of claim 36 wherein said net has a basis weight in the range of from about 0.5 to about 5.0 ounces per square yard.

37. The sanitary napkin of claim 36, wherein said net has a caliper in the range of from about 5 to about 25 mils.

38. The sanitary napkin of claim 37, wherein said net has an open area in the range of from about 30% to about 60%.

39. The sanitary napkin of claim 38, wherein said net has a mesh in the range of from about 20 to about 40.

40. The sanitary napkin of claim 39, wherein said net is comprised of filaments having a major aspect dimension in the range of from about 3 to about 12 mils.

41. The sanitary napkin of claim 40, wherein said first array of filaments is superimposed over said second array.

* * * * *